United States Patent [19]

Goto et al.

[11] 4,059,563
[45] Nov. 22, 1977

[54] NOVEL PHENOL ANTIOXIDANTS

[75] Inventors: Kuniaki Goto, Tokyo; Harumi Asai, Kamakura; Tadao Natsuume, Yokosuka, all of Japan

[73] Assignee: Nippon Zeon Co. Ltd., Tokyo, Japan

[21] Appl. No.: 722,826

[22] Filed: Sept. 13, 1976

Related U.S. Application Data

[62] Division of Ser. No. 584,931, June 9, 1975, Pat. No. 4,008,284.

[30] Foreign Application Priority Data

June 19, 1974  Japan ............................ 49-69171

[51] Int. Cl.² ............................................. C08K 5/13
[52] U.S. Cl. ............................ 260/45.95 H; 252/52 R
[58] Field of Search ............... 260/45.95 H; 252/52 R

[56] References Cited

U.S. PATENT DOCUMENTS

| | | | |
|---|---|---|---|
| 2,356,929 | 8/1944 | Hart | 260/45.95 H |
| 3,355,419 | 11/1967 | Cook | 260/45.95 H |
| 3,477,987 | 11/1969 | Hunter | 260/45.95 H |

*Primary Examiner*—V. P. Hoke
*Attorney, Agent, or Firm*—Sherman & Shalloway

[57] ABSTRACT

A phenol derivative of the general formula

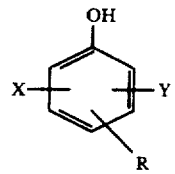

wherein R is a hydrogen atom or an alkyl group containing 1 to 4 carbon atoms, and X and Y, which may be identical or different, each represent a cyclopentyl or cyclohexyl group.

6 Claims, No Drawings

NOVEL PHENOL ANTIOXIDANTS

This is a division of application Ser. No. 584,931, filed June 9, 1975, now U.S. Pat. No. 4,008,284.

This invention relates to novel phenol derivatives, and more specifically, to novel phenol derivatives useful as additives for inhibiting the deterioration of various degradable substances such as polymeric substances (e.g., plastics or rubbers), or oily substances (e.g., lubricating oils or heat transfer media).

Generally, polymeric substances such as plastics or rubbers degrade by the action of oxygen, ozone, or light during processing or storage whereby they are colored, become opaque, and undergo urface cracking or deterioration in physical properties such as tensile strength. In order to prevent such undesirable degradation, various agents for inhibiting degradation have been developed. In particular, amine compounds, phenol compounds, sulfide compounds and phosphite compounds are generally used as anti-oxidants. The amine compounds have superior property of inhibiting degradation, but since they are susceptible to staining, they cannot be used in those fields which must avoid coloration. In these fields, therefore, the phenolic compounds or sulfide compounds such as 2,6-ditertiary butyl-p-oresol or 4,4-thiobis(6-tertiary butyl-3-methylphenol) are usually employed as antioxidants. These compounds, however, do not possess sufficient ability to inhibit degradation, and suffer from the defect that when polymeric substance containing these compounds are exposed to heat for long periods of time, they are either colored or gelled.

In the present application, the terms "degradation" and "deterioration" are used interchangeably.

It is an object of this invention to provide novel compounds which possess better ability to inhibit degradation than the conventional phenolic antioxidants, and are not susceptible to staining.

Another object of this invention is to provide a novel anti-degradative agent comprising the above compound as an active ingredient.

Other objects of this invention will become apparent from the following description.

We have found that phenol derivatives of the general formula

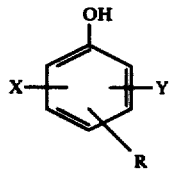

(I)

wherein R is a hydrogen atom or an alkyl group containing 1 to 4 carbon atoms, and X and Y, which may be identical or different, each represent a cyclopentyl or cyclohexyl group,
meet these objects.

Specific examples of the phenol derivatives of general formula [I] are 2,4-dicyclopentylphenol, 2,5-dicyclopentylphenol, 2,6-dicyclopentylphenol, 3,5-dicyclopentylphenol, 2,4-dicyclohexylphenol, 2,5-dicyclohexylphenol, 2,6-dicyclohexylphenol, 3,5-dicyclohexylphenol, 3,5-dicyclopentyl-p-cresol, 2,5-dicyclopentyl-p-cresol, 2,6-dicyclopentyl-p-cresol, 3,5-dicyclohexyl-p-cresol, 2,5-dicyclohexyl-p-cresol, 2,6-dicyclohexyl-p-cresol, 4,6-dicyclopentyl-o-cresol, 2,6-dicyclohexyl-o-cresol, 4-ethyl-3,5-dicyclopentylphenol, 4-ethyl-2,6-dicyclopentylphenol, 4-ethyl-3,5-dicyclohexylphenol, and 4-ethyl-2,5-dicyclohexylphenol.

Degradation of degradative substances can be effectively inhibited by adding one or more of these phenol derivatives in an amount of 0.01 to 5 parts by weight per 100 parts by weight of the degradative substances. For example, when the degradative substance is a natural or synthetic rubber, its coloration or gel formation ascribable to oxygen and/or heat can be inhibited. When the degradative substance is a plastic article, a lubricating oil or a heat transfer medium, its degradation by oxygen and/or heat can be inhibited.

Of these phenol derivatives, the cresol derivatives possess the best ability to inhibit degradation. Generally, phenol derivatives of formula [I] in which X and Y are both cyclopentyl groups have especially superior properties.

Procedures of adding the phenol derivatives to degradable substances and their amounts to be added are the same as those employed in the prior art, and if desired, known antioxidants, ultraviolet absorbers, and color inhibitors, etc. can also be used together with these phenol derivatives.

The phenol derivatives of formula [I] can be easily prepared by reacting a compound of the following formula

(II)

wherein R is a hydrogen atom or an alkyl group containing 1 to 4 carbon atoms, with at least one reagent selected from the group consisting of cyclopentadiene, cyclopentene, hydroxy-substituted cyclopentane, halogen-substituted cyclopentanes, cyclohexadiene, cyclohexene, hydroxy-substituted cyclohexane and halogen-substituted cyclohexanes in the presence of an acid catalyst such as sulfuric acid, phosphoric acid, acidic ion-exchange resins, aluminum chloride, boron trifluoride or tin chloride, and if desired, reducing the resulting product. The reaction usually ends in 30 minutes to 50 hours at 0° to 100° C. Since the reaction is performed stoichiometrically, about 2 moles of the above reagent is ordinarily used per mole of the compound of formula [II]. In some cases, about 1.5 to 3 moles of the reagent can be used per mol of the compound of formula [II].

Preferred species of the compound of formula [II] are those in which hydrogen, methyl, ethyl, propyl or butyl is bonded at the ortho-, meta- or para-position to the hydroxyl group. Specific examples include phenol, ortho-cresol, meta-cresol, para-cresol, para-ethylphenol, and meta-butylphenol. Specific examples of the above reagent are cyclopentadiene, cyclopentene, cyclopentanol, cyclopentyl chloride, cyclopentyl bromide, cyclohexadiene, cyclohexene, cyclohexanol, cyclohexyl chloride, and cyclohexyl bromide.

As the groups X and Y ascribable to the above reagent are attached to optional vacant positions of the compound of formula [II] in the above reaction, some isomers are formed simultaneously. All of the phenol derivatives of this invention resulting from the introduction of the groups X and Y into the compounds of formula [II] have superior ability to inhibit deterioration. Accordingly, if the reaction product is a mixture of such isomers, it can be directly used as an agent for inhibiting degradation without separating it into the individual isomers. On the other hand, however, if only one of the groups X and Y is introduced into the compound of formula [II], the resulting phenol derivatives have low effects of inhibiting degradation. Thus, if the reaction product contains such phenol derivatives, they must be removed by distillation prior to use as agents for inhibiting degradation.

When cyclopentadiene or cyclohexadiene is used as the reagent, the resulting compounds contain a double bond. Thus, these compounds must be saturated by reduction with hydrogen.

The phenol derivatives of this invention differ from the conventional antioxidants in that two cycloaliphatic groups (X and Y) are bonded to the benzene nucleus.

$1075 cm^{-1}$) was not seen. This analysis led to the confirmation that each of the fractions contained a hydroxyl group ascribable to the cresol, and that the fraction A was a 1,2,3,5-substituted isomer, the fraction B, a 1,2,4,5-substituted isomer, and the fraction C, a 1,2,3,5-substituted isomer.

From the results of the molecular weight measurement and the infrared absorption spectrum, it was ascertained that all of the fractions A, B and C were compounds resulting from the introduction of two cyclopentyl groups into the benzene nucleus of cresol. Furthermore, the chemical shifts of protons of the hydroxyl group and the benzene ring were determined from the nuclear magnetic resonance spectra of these fractions, and the values obtained were compared with that measured of 2,6-ditertiary butyl-p-cresol. It was found that the fraction A was 2,6-dicyclopentyl-p-cresol, the fraction B 2,5-dicyclopentyl-p-cresol, and the fraction C, 3,5-dicyclopentyl-p-cresol.

Table 1

| Fractions | Compounds | Boiling point actually measured (° C/mmHg) | Boiling point converted (° C/mmHg) | Molecular weight actually measured (average of three replicates) |
|---|---|---|---|---|
| A | 2,6-Dicyclo-* pentyl-p-cresol | 102 to 103/0.02 | 357 to 360/760 | 242 |
| B | 2,5-Dicyclo-* pentyl-p-cresol | 105 to 107/0.02 | 362 to 364/760 | 241 |
| C | 3,5-Dicyclo-* pentyl-p-cresol | 114 to 117/0.02 | 372 to 380/760 | 245 |

* The molecular weight of each dicyclopentylcresol is 244.

Because of this, they have very good ability to inhibit degradation. For example, the phenol derivatives of this invention have far superior ability to inhibit degradation to 2,6-ditertiary butyl-p-cresol which has been widely used as an antioxidant, and better ability to inhibit degradation than 2-tertiary-6-cyclopentyl-p-cresol recently developed (see Japanese Patent Publication No. 19332/72).

The phenol derivatives of this invention can find utility not only as agents for inhibiting deterioration, especially anti-oxidants, but also as polymerization inhibitors.

The following non-limitative Examples specifically illustrate the present invention. In all of the Examples, the parts indicated are by weight.

EXAMPLE 1

A 5-liter glass flask was charged with 1081 g of p-cresol and 300 g of a strongly acidic ion-exchange resin (Amberlyst-15, trademark for a product of Rohm and Haas), and 1360 g of cyclopentene was added gradually. This mixture was heated at 75° to 80° C. for 20 hours with stirring. The resulting reaction mixture was filtered to separate the catalyst. The filtrate was distilled at reduced pressure to separate three fractions shown in Table 1. The molecular weight of each of these fractions was measured by vapor pressure osmometry. The results are shown in Table 1. These fractions were all viscous oils at room temperature, and the total yield of these three fractions was more than 88% based on the cyclopentene.

Analysis of these three fractions by an infrared absorption spectrum showed that an absorption of a hydroxyl group appeared at 3500 to 3550 $cm^{-1}$, but an absorption of an ether linkage (at 1250 $cm^{-1}$ and 1020 to

EXAMPLE 2 p-Cresol was reacted with cyclopentene under quite the same conditions as in Example 1. The resulting reaction mixture was filtered to separate the catalyst. The filtrate was distilled at reduced pressure to separate a fraction (fraction D) having a boiling point of 102° to 117° C/0.02 mmHg. As is clear from Example 1, this fraction is a mixture of 2,6-dicyclopentyl-p-cresol, 2,5-dicyclopentyl-p-cresol and 3,5-dicyclopentyl-p-cresol, and is a viscous oily product at room temperature.

EXAMPLE 3

30 g of a strongly acidic ion exchange resin was added to 100 g of p-cresol, and while heating the mixture at 70° to 80° C. with stirring, 155 g of cyclohexene was gradually added dropwise. After the addition, the mixture was further stirred for 24 hours. The reaction mixture obtained was filtered to separate the catalyst. The filtrate was distilled at reduced pressure to separate three fractions shown in Table 2. All of these fractions were syrupy products at room temperature. The total yield of the three fractions was 80% based on the cyclohexene.

These fractions were analyzed in the same way as in Example 1, and it was found that the fraction E was 2,6-dicyclohexyl-p-cresol, the fraction F, 2,5-dicyclohexyl-p-cresol, and the fraction G, 3,5-dicyclohexyl-p-cresol.

Table 2

| Fractions | Compounds | Boiling point (° C/mmHg) | |
|---|---|---|---|
| | | Actually measured | Converted |
| E | 2,6-Dicyclohexyl-p-cresol | 124–126/0.03 | 385–387/760 |
| F | 2,5-Dicyclohexyl-p-cresol | 128–131/0.03 | 392–396/760 |
| G | 3,5-Dicyclohexyl-p-cresol | 132–138/0.03 | 398–407/760 |

EXAMPLE 4 p-Cresol was reacted with cyclohexene under quite the same conditions as in Example 3. The resulting reaction mixture was filtered to separate the catalyst. The filtrate was distilled at reduced pressure to separate a fraction (fraction H) having a boiling point of 124° to 138° C./0.03 mmHg. As is clear from Example 3, this fraction was a mixture of 2,6-dicyclohexyl-p-cresol, 2,5-dicyclohexyl-p-cresol and was 3,5-dicyclohexyl-p-cresol, and a syrupy substance at room temperature.

EXAMPLE 5

2.0 parts of each of the fractions A, B and C obtained in Example 1 was added to 100 parts, calculated as rubber content, of an acrylonitrile-butadiene rubber latex (combined acrylonitrile 33%, solids concentration 29%). By a customary procedure, the latex was coagulated. The coagulated product was dried at 50° C. under reduced pressure for 24 hours to afford a solid rubber. 5.0 parts of zinc oxide, 0.3 parts of sulfuric acid, 1.0 part of stearic acid, 40.0 parts of FEF carbon black, 3.0 parts of tetraethylthiuram disulfide and 2.5 parts of N-cyclohexylbenzothiazole sulfenamide were compounded with 100 parts of the resulting rubber. The compounded mixture was heated at 160° C. for 20 minutes. Test pieces were prepared from the vulcanized rubber, and their properties in the normal state and after aging were measured. The heat deterioration test was performed in accordance with the test tube heat deterioration method specified in JIS-K 6301 whereby the test pieces were allowed to stand in a metal block heating medium heated at 140° C. for a prescribed period of time (1 day, 3 days, 5 days). The results obtained are shown in Table 3.

EXAMPLE 6

A graft copolymer latex was prepared by graft copolymerizing 30 parts of methyl methacrylate and 30 parts of styrene with a styrene-butadiene latex in an amount of of 100 parts calculated as solids content. 3.0 parts each of the fractions A, B and C obtained in Example 1 was added to the above graft copolymer latex in an amount corresponding to 100 parts of the rubber content. The latex was coagulated with aluminum sulfate, and heated at 90° to 95° C. for 5 minutes to flocculate and dehydrate it and to obtain a wet cake with a heat loss of 45 to 50%. The wet cake was stuffed lightly into a basket having a capacity of 5.5 cm³ and made of a 80-mesh wire gauze, and placed in a gear-type aging tester. The time that passed until the ignition of the sample was measured. The measurement was made three times, and an average value of the three replicates is shown in Table 4.

Table 4

| | Examples of the invention | | | Control |
|---|---|---|---|---|
| | Fraction A | Fraction B | Fraction C | BHT |
| Time required until ignition | 4.25 | 4.45 | 4.50 | 1.75 |

The above results demonstrate that the phenol derivatives of this invention have far superior effects of inhibiting heat deterioration to the conventional phenolic antioxidants.

EXAMPLE 7

2.0 parts each of the fractions A, B and C obtained in Example 1 was added to 100 parts, as rubber content, of a styrene/butadiene rubber latex (combined styrene 23.3%, solids concentration 27%), and then the latex was coagulated with 5% saline solution and 1% sulfuric acid. The coagulated product was dried at 50° C. for 20 hours under reduced pressure to form a solid rubber.

The rubber obtained was allowed to stand for a prescribed period of time in a gear-type aging tester held at 90° C. ± 1° C., and the gel content of each of the samples was measured. The measurement of the gel content was performed by placing 0.2 g of the rubber in a basket made of a 80-mesh stainless steel wire gauze, immersing the basket in 100 ml. of toluene for 24 hours, and then measuring the amount of the rubber remaining in the Table 3

| | | | Examples of the invention | | | Control |
|---|---|---|---|---|---|---|
| | | | Fraction A | Fraction B | Fraction C | BHT* |
| In the normal state | | Elongation (%) | 340 | 380 | 390 | 360 |
| | | Hardness (JIS) | 68 – 65 | 69 – 65 | 69 – 65 | 68 – 64 |
| After heat deterioration | 1 day | Elongation (%) | 240 | 270 | 250 | 280 |
| | | Change in elongation (%) | −33.3 | −28.9 | −35.9 | −22.2 |
| | | Hardness (JIS) | 71 – 63 | 71 – 68 | 71 – 67 | 71 – 67 |
| | | Change in Hardness (JIS) | +3/−1 | +2/+3 | +2/+2 | +3/+3 |
| | 3 days | Elongation (%) | 140 | 140 | 140 | 120 |
| | | Change in Elongation (%) | −58.8 | −63.2 | −64.1 | −66.7 |
| | | Hardness (JIS) | 72 – 69 | 72 – 69 | 71 – 69 | 70 – 68 |
| | | Change in Hardness (JIS) | +4/+5 | +3/+4 | +2/+4 | +2/+4 |
| | 5 days | Elongation (%) | 60 | 50 | 60 | 30 |
| | | Change in Elongation (%) | −82.4 | −86.8 | −84.6 | −91.7 |
| | | Hardness (JIS) | 80 – 78 | 80 – 78 | 77 – 75 | 80 – 78 |
| | | Change in Hardness (JIS) | +12/++14 | +11/+13 | + 8/+10 | +12/+14 |

*2,6-ditertiary butyl-p-cresol basket. Coloration of the rubber was also examined in the heat aging test. The results are shown in Table 5.

Table 5

| Heating time (hours) | Examples of the invention | | | Control examples | |
|---|---|---|---|---|---|
| | Fraction A | Fraction B | Fraction C | Not added | BHT |
| 0 | 0.6% | 0.6% | 0.6% | 0.7% | 0.6% |
| 5 | 0.6 | 0.6 | 0.6 | 28.7 | 0.7 |
| 10 | 0.7 | 0.6 | 0.7 | 57.1 | 0.7 |
| 24 | 0.7 | 0.8 | 0.8 | 65.0 | 60.6 |
| 48 | 1.2 | 1.0 | 0.9 | 77.0 | 74.0 |
| coloration of rubber | None | None | None | Colored yellow in 5 hours | Colored yellow in 24 hours |

The results shown in Table 5 demonstrate that gel formation or coloration was scarcely observed with the styrene-butadiene rubbers containing the phenol derivative of this invention even after allowing them to stand for 48 hours in a heat aging tester. On the other hand, the rubber containing 2,6-ditertiary butyl-p-cresol, a conventional non-staining antioxidant, yielded a great amount of gel at the end of 24 hours, and was colored yellow. Accordingly, it shows that the phenol derivatives of this invention have very superior ability to inhibit the deterioration of rubber.

EXAMPLE 8

A compounded mixture of the styrene/butadiene rubber and the deterioration inhibiting agent was prepared in the same way as in Example 7 except that the fraction D as a deterioration inhibiting agent was used in varying amounts shown in Table 6 per 100 parts by weight of the rubber. The resulting compounded mixtures were also tested for heat deterioration. The results are shown in Table 6.

Table 6

| Anti-degradative agent | | Amount (parts) | 0.2 | | | 0.5 | | | 1.0 | | |
|---|---|---|---|---|---|---|---|---|---|---|---|
| | | Heating time (hr) | 24 | 48 | 96 | 24 | 48 | 96 | 24 | 48 | 96 |
| Invention Fraction D | Percent gel formation(%) | | 0.5 | 0.8 | 0.8 | 0.6 | 0.7 | 0.7 | 0.6 | 0.7 | 0.7 |
| | Coloration of rubber | | No | No | Slightly yellow | No | No | Slightly yellow | No | No | Slightly yellow |
| Control BHT | Percnet gel formation(%) | | 68.0 | 75.0 | 78.5 | 60.1 | 72.0 | 72.0 | 63.4 | 75.9 | 76.9 |
| | Coloration of rubber | | Yellow | Brown | Brown | Yellow | Yellow | Brown | Yellow | Yellow | Yellow |

The results obtained show that the phenol derivatives of this invention exhibit very good anti-degradative effects even when used in widely varying proportions relative to the rubber.

EXAMPLE 9

A compounded mixture of styrene/butadiene rubber and an anti-degradative agent was prepared in the same way as in Example 7 except that the fraction D obtained in Example 2, the fraction E obtained in Example 3 and the fraction H obtained in Example 4 were used respectively as the anti-degradative agent in varying amounts per 100 parts of the rubber as shown in Table 7, and the heat deterioration test was performed at 120° C. The results are shown in Table 7.

Table 7

| Amount (parts) | Heating time (hr) | Examples of the Invention | | | | | | Controls | |
|---|---|---|---|---|---|---|---|---|---|
| | | Fraction D | | Fraction E | | Fraction H | | BHT | |
| | | Percent gel formation | Coloration | Percent gel formation | Coloration | Percent gel formation | Coloration | Percent gel formation | Coloration |
| 0.1 | 2 | 0.9% | No | 3.6% | No | 4.4% | No | not measured | Light yellow |
| | 4 | 0.9 | No | 23.8 | No | 27.3 | No | | Light yellow |
| | 8 | 1.0 | Slightly yellow | 27.2 | Slightly yellow | 29.5 | Slightly yellow | | Yellow |
| 0.5 | 2 | 0.9 | No | 0.8 | No | 0.8 | No | 4.0 | Light yellow |
| | 4 | 0.9 | Slightly yellow | 1.0 | No | 0.8 | No | 12.1 | Light yellow |
| | 8 | 1.0 | Slightly yellow | 3.3 | Slightly yellow | 2.4 | Slightly yellow | 68.2 | Yellow |
| 1.0 | 2 | 1.1 | No | 1.0 | No | 0.8 | No | 0.8 | Light yellow |
| | 4 | 1.0 | No | 1.6 | Slightly yellow | 1.2 | No | 9.7 | Light yellow |
| | 8 | 3.7 | Light yellow | 11.3 | Light yellow | 6.7 | Light yellow | 68.2 | Yellow |

It can be seen from these results that the fractions E and H have superior ability to inhibit degradation same as the fraction D.

The anti-degradative properties of the fractions F and G obtained in Example 3 were also measured, and it was found that these fractions also exhibit almost equivalent effects to the fraction E.

EXAMPLE 10

The fraction D obtained in Example 2 was added to a styrene/butadiene rubber latex in the same way as in Example 7. The latex was coagulated, and dried to form a solid rubber. A prescribed amount of the rubber was dissolved in benzene, and the resulting rubber solution was coated on a glass sheet. By volatilizing the benzene in an atmosphere of nitrogen, a film was formed.

The glass sheet coated with this rubber film was placed in an oxygen absorption measuring device (a test tube with a diameter of 30 mm containing a small amount of molecular sieve, to which a manometer was connected through a glass tube). The inside of the device was purged with oxygen. The test tube portion of the device was placed in a constant temperature tank heated at 130° C., and the amount of oxygen absorbed as a result of the deterioration of the rubber film was measured periodically starting 10 minutes after placing the test tube in it. The results are shown in Table 8. The results of measurement were expressed in terms of the time required to absorb 20 cc of oxygen per gram of the rubber.

Tab;e 8

| Amount (parts) | Invention Fraction D | Control BHT |
|---|---|---|
| 0.2 | 93 hours | 55 hours |
| 1.0 | 222 hours | 193 hours |

EXAMPLE 11

Glass fibers each with a diameter of 10 μ were immersed in a benzene solution of the same styrene-butadiene rubber (containing an antioxidant) as obtained in Example 10, and the benzene was volatilized in an atmosphere of nitrogen to form rubber-coated glass fibers. The resulting glass fibers were placed in the same oxygen absorption measuring device as used in Example 10, and the test tube portion of the device was placed in a constant temperature tank heated at 120° C.. The amount of oxygen absorbed as a result of the deterioration of the rubber was measured periodically. The results are shown in Table 9. The results were expressed in terms of the time required to absorb 10 cc of oxygen per gram of the rubber.

Table 9

| Amount (parts) | Invention Fraction D | Controls 2-tertiary-butyl-6-cyclopentyl-p-cresol | BHT |
|---|---|---|---|
| 0.1 | 33 min. | 24 min. | not measured |
| 0.3 | 52 min. | 37 min. | 9 min. |

These results demonstrate that the fraction D has superior ability to inhibit deterioration to the 2-tertiary butyl-6-cyclopentyl-p-cresol which is evaluated as a compound having good ability to inhibit deterioration.

What we claim is:

1. In a process for inhibiting the deterioration of degradable polymeric and oily substances by adding an antidegradation agent to said degradable substance the improvement which comprises adding to said degradable substance from 0.01 to 5 parts by weight per 100 parts by weight of the degradable substance of at least one p-cresol compound of the formula:

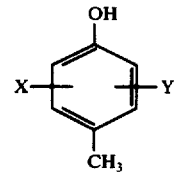

wherein X and Y each represent a cyclopentyl group.

2. The process of claim 1 wherein said compound is 2,6-dicyclopentyl-p-cresol.

3. The process of claim 1 wherein said compound is 2,5-dicyclopentyl-p-cresol.

4. The process of claim 1 wherein said compound is 3,5-diclyclopentyl-p-cresol.

5. The process of claim 1 wherein said degradable substance is natural or synthetic rubber.

6. The process of claim 5 wherein said degradable substance is a synthetic rubber which comprises styrene-butadiene rubber or acrylonitrile-butadiene rubber.

* * * * *